US005599617A

United States Patent [19]

Ewald

[11] Patent Number: 5,599,617
[45] Date of Patent: Feb. 4, 1997

[54] NONSLIP ARTICLE SUPPORT PAD

[75] Inventor: Michael A. Ewald, Highland Village, Tex.

[73] Assignee: Struckmeyer Corporation, Dallas, Tex.

[21] Appl. No.: 510,520

[22] Filed: Aug. 2, 1995

[51] Int. Cl.$^6$ ............................................. B32B 7/12
[52] U.S. Cl. ................................ 428/317.3; 428/317.7; 428/354
[58] Field of Search ........................... 428/317.3, 308.4, 428/317.1, 317.7, 319.7, 319.3, 339, 354

[56] References Cited

U.S. PATENT DOCUMENTS

| | | | |
|---|---|---|---|
| 3,380,582 | 4/1968 | Moyer, Jr. et al. | 428/317.3 X |
| 3,629,051 | 12/1971 | Mitchell | 161/162 |
| 3,665,918 | 5/1972 | Lindquist et al. | 428/317.3 X |
| 3,972,328 | 8/1976 | Chen | 128/156 |
| 4,316,926 | 2/1982 | Kaminstein | 428/354 X |
| 4,552,802 | 11/1985 | Mechin | 428/317.3 X |
| 4,705,715 | 11/1987 | DeCoste, Jr. et al. | 428/317.3 X |
| 4,743,499 | 5/1988 | Volke | 428/317.3 |
| 5,128,187 | 7/1992 | Polski | 428/317.3 X |

*Primary Examiner*—Daniel Zirker
*Attorney, Agent, or Firm*—Jenkens & Gilchrist

[57] ABSTRACT

A conformable, nonslip article support pad has a flexible substrate formed of a resiliently compressible foam material and a flexible film bonded onto an upper surface of the foam substrate. The flexible film forms an upper surface on the article support pad that has a kinetic coefficient of friction with steel that is greater than 1.0 and, in cooperation with the substrate, forms a drapable structure having a readily deformable, slip-resistant, upper surface. The article support pad will maintain an article placed thereon at its initial position even though the surface of the support pad is tilted by as much as 78° from a horizontal plane.

5 Claims, 1 Drawing Sheet

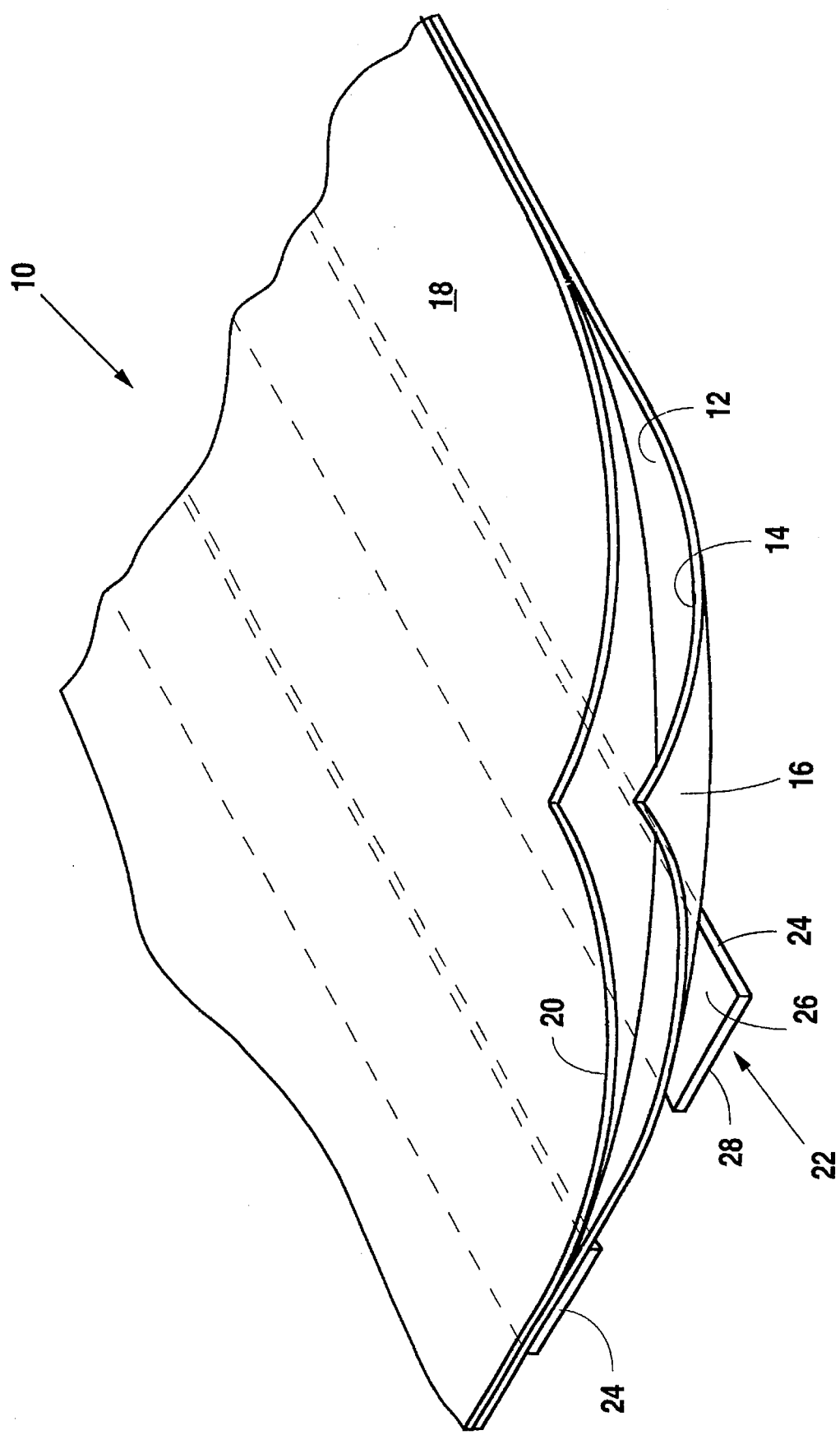

NONSLIP ARTICLE SUPPORT PAD

FIELD OF THE INVENTION

This invention relates generally to article support pads having a nonslip surface, and more particularly to such pads that are drapable and readily conformable to an underlying recumbent surface.

BACKGROUND ART

Support pads for temporary retention of various articles are used in many fields of application. For example, landing or holding pads for surgical instruments are common fixtures in operating rooms, being generally placed adjacent the surgical site so that the surgeon and nurse can easily reach surgical instruments either before, during, or after use. In such surgical applications, the accepted technique for passing surgical instruments requires that the instrument be placed on an instrument pad by the scrub nurse, after which the surgeon picks up the instrument from the pad. Conversely, the surgeon is required to place the operating instrument on the pad for pick up by the scrub nurse rather than hand it directly to the nurse, assistant, or attendant. This technique reduces the possibility of skin puncture by sharp surgical instruments.

The early instrument pads were made by the scrub nurses. They would double a towel or use two unfolded towels, one on top of the other, and place them adjacent the surgical site, usually on top of the surgical drape coveting the patient. More recently, instrument pads have been fabricated from rubber, sheet foam, or a combination of sheet foam and magnets. For example, a reusable silicon instrument holding drape is produced by TAUB Industries under the trademark INSTA-HOLD™. However, these drapes are relatively expensive and require sterilization and storage in a sterile environment between each use. Additionally, it has been found that the silicon surface provides only limited retention of surgical instruments placed on the pad, occasionally allowing the surgical instruments to roll and fall onto the operating room floor.

Magnetic instrument pads, are commercially available and generally consist of four components; polyurethane foam, a plurality of flexible magnets, polyethylene film encasing the magnets, and a plurality of steel shims positioned between the magnets and the foam to enhance the magnetic properties of the magnets and make the magnets more rigid. Thus, magnetic pads are relatively heavy and have limited drapability. Also, many surgical instruments are now formed of stainless steel, plastic, ceramic, composite materials, or other nonmagnetic materials and, therefore, are not magnetically retained on the pad. Additionally this pad, as a result of the required multiple magnets and shims, has significant fabrication costs and, accordingly, is relatively expensive to produce.

Surgical instrument holding pads have also been provided as a single layer of polymer foam such as polyolefin or polyethylene. These single component pads generally provided good drapability, conformity with an undersurface, and an upper surface that was easily deformed to provide a cushioned depository for the instruments placed thereon. The single layer polymer foam pads are economical to produce, but it has been found that surgical instruments tend to slip or roll when the upper surface of the pad is angled away from a horizontal plane. None of the nonmagnetic instrument pads are capable of preventing slippage of surgical instruments if the surface is tilted more than 45° from horizontal, i.e., none of the non-magnetic instrument pads have a kinetic coefficient of friction (surface to steel) that is greater than 1.

The present invention is directed to solving the problems set forth above. It is desirable to have a pad for retaining surgical instruments, or other articles, in their placed position even though the surface of the pad may be disposed at an angle exceeding 45° from a horizontal plane. It is also desirable that such an article support pad be readily conformable with an underlying surface on which it may be placed, and provide a cushioned, locally deformable repository for instruments or other articles placed thereon. Furthermore, it is desirable that such a pad be relatively inexpensive to produce so that it can be disposed of after each use. Still further, it is desirable to have such a pad that is readily attachable to a selected underlying surface, such as a surgical drape.

SUMMARY OF THE INVENTION

In accordance with one aspect of the present invention, a conformable, nonslip article support pad has a flexible substrate formed of a resiliently compressible foam material, and a flexible film bonded to an upper surface of the flexible substrate and having a kinetic coefficient of friction with steel that is greater than 1.0. The flexible substrate and flexible film cooperate to form a drapable structure having a readily deformable slip-resistant upper surface.

Another feature of the article support pad embodying the present invention includes a means for removably attaching a lower surface of the pad to a selected surface.

BRIEF DESCRIPTION OF THE DRAWING

The single figure is a perspective view of the article support pad embodying the present invention with the principal elements of the laminated pad partially separated at one corner for description purposes.

BEST MODE FOR CARRYING OUT THE INVENTION

As shown in the accompanying drawing, a conformable, nonslip article support pad embodying the present invention is generally indicated by the reference numeral 10. The article support pad 10 has a flexible substrate 12 formed of a resiliently compressible foam material having an upper surface 14 and a lower surface 16. Preferably, the substrate 12 is formed of open cell polyurethane foam having a cell count of from about 55 to about 65 pours per inch and a density of from about 1.35 lbs/ft$^3$ (21.6 kg/m$^3$) to about 1.65 lbs/ft$^3$ (26.4 kg/m$^3$). Closed cell foam materials may also be used but are generally have less ability to drape, i.e., hang in loose folds or conform to an underlying surface in a cloth-like manner. The foam substrate desirably has a noncompressed, or free state, thickness of from about 0.03 in (0.79 mm) to about 0.25 in (6.35 mm), and preferably about 0.094 in (2.38 mm).

The article support pad 10 also has a flexible film 18 that is bonded, in the manner described below, to the upper surface 14 of the flexible substrate 12 to form a single integral structure that essentially has the same drapability as the flexible substrate 12 by itself, and an upper surface 20 that is highly slip-resistant and readily deformable by an article resting on the upper surface 20. The term "readily deformable", as used herein and in the claims, means that the surface is capable of being locally compressed when impacted by an article dropped or forcedly deposited on the surface, i.e., it is a cushioned surface.

The flexible film 18 is advantageously formed of a material that will provide a slip-resistant upper surface 20 on the support pad 10. It is desirable that the kinetic coefficient of friction (surface to steel) of the upper surface 20 be greater than 1, i.e., be at least capable of maintaining an article previously disposed on the surface 20 at rest when the upper surface 20 is tilted 45° from a horizontal plane. When constructed according to the preferred embodiment of the present invention described herein, it has been discovered that the upper surface 20 of the support pad 10 has a kinetic coefficient of friction (surface 20 to steel) of about 4.7. Various steel surgical instruments, such as clamps, tweezers and the like were deposited on the upper surface 20 of the pad, and the pad was tilted to a measured angle of 78° from the initial horizontal plane before any slippage of the instruments was observed.

In the preferred embodiment of the present invention, the flexible film 18 is an elastomeric material comprising a mixture of polyethylene and thermoplastic rubber. More specifically, the thermoplastic rubber is a block polymer comprising, by weight, from about 55% to about 65% styrene-butadiene-styrene block copolymer, from about 30% to about 40% mineral oil, and from 0% to less than 1% each of zinc stearate, magnesium carbonate, calcium stearate, antioxidants and stabilizers, and commercially available from Shell Oil Company under the trademark KRAYTON™ DRP 6020. This material, along with the other materials comprising the preferred embodiment of the present invention, has been approved by the Food and Drug Administration branch of the U.S. Department of Health and Human Services for use in medical environments such as operating rooms. Other materials, such as olefinic and styrenic elastomers, and polyester and polyether urethane elastomers, may be suitable as components of the flexible film 18, but have not been submitted for FDA approval as components of the article support pad 10 embodying the present invention. Other materials, such as high-tack latex rubber should be avoided if the pad is to be used in medical applications due to the allergic reaction some people incur when they come in contact with, or in close proximity to, latex products.

Desirably, the conformable, nonslip article support pad 10 embodying the present invention includes a means 22 for removably attaching the lower surface 16 of the substrate 12 to a selected surface upon which the support pad 10 is recumbent, or resting. For example, in the surgical instrument pad illustrative of the preferred embodiment of the present invention, the recumbent surface is typically a surgical drape covering the patient. In the preferred embodiment of the present invention, the means 22 for removably attaching the lower surface 16 of the substrate 12 to a selected surface comprises one or more strips 24 of a double-coated tape formed of plastic film, such as polyester or polyethylene, having a thickness of about 0.5 mils (0.013 mm). The strips of plastic film 24 have an upper surface 26 and a lower surface 28, both of which are coated with a high tack rubber based adhesive. The adhesive on the first surface desirably has a thickness of about 1.5 mils (0.038 mm) and advantageously joins the plastic strips 24 to the lower surface 16 of the flexible substrate 12. The adhesive coating on the second, or lower, surface 28 of the plastic strips 24 desirably has a thickness of about 1.35 mils (0.034 mm) and is protected until ready for use by a conventional silicon-coated paper release liner, not shown. When the release liner is removed, the adhesive coating on the second surface 28 of the strips of the plastic film 24 is exposed, providing a temporary adhesive connection between the lower surface 16 of the substrate 12 and the selected recumbent surface, upon contact of the article support pad 10 with the recumbent surface.

Alternatively, the means 22 for removably attaching the lower surface 16 of the substrate 12 to a selected surface may comprise an adhesive coating deposited directly onto selected portions, or all, of the lower surface 16 of the flexible substram 12 and protected by release paper until ready for use. Other means such as interlocking hook and loop fabric may also be used for removably attaching the lower surface 16 of the substrate 12 to a selected underlying surface.

The article support pad 10 embodying the present invention is preferably formed by roll casting the flexible film 18 directly onto the upper surface 14 of the flexible foam substrate 12. Preferably, the flexible foam substrate is provided in roll form having a width of up to 60 in (1.524 m). In the illustrative example presented herein the flexible foam substrate is provided in a roll having a width of about 20 in (50.8 cm). The roll of flexible foam is unwound and fed to the infeed roller of a conventional roll caster. The thermoplastic elastomeric material forming the flexible film 18 is heated to its melting temperature, cast directly onto the flexible foam substram, and spread evenly over the upper surface 14 of the substrate 12 by the action of the rollers. The polyurethane foam material forming the flexible substrate 12 typically has a melting temperature of from about 500° F. (260° C.) to about 530° F. (277° C.), and therefore, to avoid thermal decomposition of the substrate during processing, it is necessary that the molten elastomeric material forming the flexible film 18 not be deposited on the substrate at a temperature higher than 500° F. (260° C.), and preferably not above about 450° F. (232° C.). The liquid elastomer is applied on the upper surface 14 of the foam substrate 12 at a rate sufficient to provide a film thickness of from about 2 mils (0.05 mm) to about 8 mils (0.2 mm), and preferably about 6 mils (0.15 mm). Alternatively, the flexible foam-film laminated structure may be formed by other methods, such as adhesively or thermally joining a preformed flexible film to the foam substrate.

After roll casting, the composite film surfaced foam substrate is laminated, sealed and cut to size in a heated die press wherein it is maintained, under an applied pressure, at a temperature of about 350° F. (177° C.) for about 4 seconds. After heat pressing, the die press cuts the roll into separate pans of a predetermined size. In the illustrative example described herein, an 8-ton press is used to laminate and heat seal the foam and film and then cut the laminated material into rectangularly shaped forms measuring about 20 in (50.8 cm) by 30 in 76.2 cm). During the above process steps, the liquid elastomer of the flexible film somewhat penetrates the cells of the flexible foam substram and, upon solidification, forms an intimate, inseparable bond between the flexible film 18 and the foam substrate 12.

The double-stick strips of plastic film 24 are preferably applied after lamination of the flexible slip-resistant film 18 to the foam substram 12. In the illustrative example described herein, the strips of plastic film 24 are applied after the laminated material is cut into the preform shapes. However, if desired, the adhesive strips 24 may be applied to the lower surface 16 of the foam substrate 12 after lamination, while still in roll form, prior to cutting into discreet members. After attachment of the release liner, which preferably has a width somewhat greater than the width of the adhesive strip 24, to the lower surface 28 of the strip 24, the preformed rectangular shape may, if required, be further trimmed to a desired shape or dimension. The completed instrument support pad 10 is then folded, placed in appropriate packaging and, if desired, sterilized prior to delivery and use.

Industrial Applicability

The conformable, nonslip article support pad 10 embodying the present invention is particularly suitable for use as a landing and/or holding pad for surgical instruments during a surgery. The article support pad 10 will maintain surgical instruments deposited on the pad at their initial position, even when the pad is unevenly disposed over a surgical drape covering a patient's body. In particular, it has been found that the article support pad 10, when constructed in accordance with the above described preferred embodiment, provides a slip-resistant upper surface 20 that maintains surgical instruments at the deposited position even though the surface on which they are resting is tilted up to 78° from a horizontal plane. Thus, the surgical instruments are prevented from rolling, and possibly falling onto unsterilized surfaces, during "no-touch" transfer of the instruments between surgeon and attendant.

The nonslip article support pad 10 embodying the present invention is economical to produce and therefor is disposable after use without incurring disadvantageous cost penalties. Additionally, the article support pad 10 provides a highly slip-resistant surface having a kinetic coefficient of friction (surface to steel) greater than 1 and, as measured by actual test, up to 4.7. These important advantages enable the article support pad 10 to be advantageously used in many other applications for supporting items that may be subjected to tilting or sliding. For example, the article support pad 10 is particularly useful as a disposable mat that provides a nonslip surface for food trays, beverages and the like. Thus, the article support pad 10 is also useful as a tray or table mat, or as a tray, shelf or bin liner, especially on airplanes, ships, cars and other vehicles.

Other aspects, features and advantages of the present invention can be obtained from a study of this disclosure and the appended claims.

What is claimed is:

1. A conformable, nonslip article support pad, comprising:
   it flexible substrate formed of a resiliently compressible foam material having defined upper and lower surfaces;
   a flexible film having a kinetic coefficient of friction with steel that is greater than 1.0, said film being bonded to the upper surface of said flexible substrate forming an integral structure therewith and cooperating with the substrate to form a drapable structure having a readily deformable slip-resistant upper surface; and
   a means for removably attaching the lower surface of the substrate of said pad to a selected recumbent surface, said means comprising a plastic film having first and second surfaces, said first surface being adhesively bonded to the lower surface of said flexible substrate and said second surface having an adhesive coating predisposed thereon and adapted to provide a temporary adhesive connection between said lower surface of the substrate and said selected recumbent surface when said article support pad is placed in contact with said selected recumbent surface.

2. A conformable, nonslip article support pad, as set forth in claim 1, wherein the resiliently compressible foam material comprising the substrate is polyurethane foam having a density of from about 1.35 lbs/ft$^3$ (21.6 kg/m$^3$) to about 1.65 lbs/ft$^3$ (26.4 kg/m$^3$).

3. A conformable, nonslip article support pad, as set forth in claim 2, wherein said substrate has an noncompressed thickness of from about 0.03 in (0.79 mm) to about 0.25 in (6.35 mm).

4. A conformable, nonslip article support pad, as set forth in claim 1, wherein said flexible film bonded to the upper surface of said substrate is formed of an elastomeric material.

5. A conformable, nonslip article support pad, as set forth in claim 1, wherein said plastic film having a first surface adhesively bonded to the lower surface of said flexible substrate is formed of a material selected from the group consisting of polyester and polyether.

* * * * *

UNITED STATES PATENT AND TRADEMARK OFFICE
CERTIFICATE OF CORRECTION

PATENT NO. : 5,599,617
DATED : February 4, 1997
INVENTOR(S) : Michael A. Ewald

It is certified that error appears in the above-indentified patent and that said Letters Patent is hereby corrected as shown below:

Col. 1, line 30          "coveting" should be "covering"

Col. 4, line 9           "substram" should be "substrate"

Col. 4, line 25          "substram" should be "substrate"

Col. 4, line 53          "substram" should be "substrate"

Col. 4, line 58          "substram" should be "substrate"

Col. 6, line 3           "it" should be "a"

Signed and Sealed this

Twenty-fifth Day of November, 1997

Attest:

BRUCE LEHMAN

Attesting Officer    Commissioner of Patents and Trademarks